United States Patent [19]

Sorochenko

[11] Patent Number: 4,671,274
[45] Date of Patent: Jun. 9, 1987

[54] BIPOLAR ELECTROSURGICAL INSTRUMENT

[75] Inventor: Oleg A. Sorochenko, Kharkov, U.S.S.R.

[73] Assignee: Kharkovsky Nauchno-Issledovatelsky Institut Obschei I, U.S.S.R.

[21] Appl. No.: 783,930

[22] PCT Filed: Jan. 30, 1984

[86] PCT No.: PCT/SU84/00004
§ 371 Date: Sep. 25, 1985
§ 102(e) Date: Sep. 25, 1985

[87] PCT Pub. No.: WO85/03214
PCT Pub. Date: Aug. 1, 1985

[51] Int. Cl.⁴ ............................................. A61B 17/36
[52] U.S. Cl. ............................ 128/303.14; 128/303.17
[58] Field of Search ................... 128/303.13, 303.14, 128/303.15, 303.16, 303.17, 321, 322, 749, 800

[56] References Cited

U.S. PATENT DOCUMENTS 1,496,438  6/1924  Wallerich ..................... 128/303.14
1,852,542  4/1932  Sovatkin ............................ 128/322
1,918,889  5/1932  Bacon ................................. 128/322
2,002,594  3/1933  Wappler et al. ............... 128/303.15
4,085,756  4/1978  Weaver .......................... 128/303.14

FOREIGN PATENT DOCUMENTS 1152220  4/1958  Fed. Rep. of Germany ...... 128/322
  76419  9/1949  U.S.S.R. .
 401367 10/1973  U.S.S.R. .

*Primary Examiner*—Kyle L. Howell
*Assistant Examiner*—Randy Citrin
*Attorney, Agent, or Firm*—Fleit, Jacobson, Cohn & Price

[57] ABSTRACT

A bipolar electrosurgical instrument, comprising movable arms (1 and 3) electrically insulated from each other and provided with current-carrying working jaws. According to the invention, the working jaws are shaped as prongs (6 and 7) curved in the same direction, the prongs (7) of the working jaw of the arm (3) being shaped as a fork, which enables one to manipulate in a bloodless operative field of the various parenchymatous organs due to quick and reliable fusion of nonopened (intact) large-calibre blood vessels over a preset segment length thereof.

8 Claims, 14 Drawing Figures

BIPOLAR ELECTROSURGICAL INSTRUMENT

TECHNICAL FIELD

The present invention relates generally to medicine, more specifically to surgery, and is particularly concerned with bipolar electrosurgical instruments.

The invention can find widespread application for surgery in the most diverse anatomical regions of the human body involving the use of r.f. electrosurgery for electrotomy and electrocoagulation of living tissues within a board frequency range. The bipolar electrosurgical instrument of the present invention enables one to successfully perform such surgical procedures as, e.g., severing or resection of tissues by the electrotomy technique; slitting open thick-walled organs, e.g., the stomach, intestines, urinary bladder, and the like; severing and coagulation of blood vessels of any calibre, and so on.

The bipolar electrosurgical instrument of the invention can find most utility when applied for performing bloodless surgical procedures on parenchymatous organs, such as the liver, spleen, kidneys, etc., as well as for handling blood vessels of the most diverse calibres.

BACKGROUND ART

High-frequency electrosurgery belongs to such techniques that are now indispensable in performing most diverse operative procedures in general surgery, onco- and neurosurgery, gastoenterology, urology, ophthalmosurgery, and in many other branches of clinical medicine.

High-frequency electrosurgery is understood to mean a method of surgical effect with an r.f. current produced on the tissue of a patient's body with the purpose of its dissecting or coagulation. The method is based on physical and chemical processes proceeding in body tissues and evoked chiefly by the diathermic current effect.

High-frequency electrosurgery falls into two types, viz, monopolar and bipolar.

In case of monopolar electrosurgery one of the electrodes is active since the maximum current density is developed thereon, whereby this electrode is a working tool, while the other (auxiliary) electrode is passive.

In case of bipolar electrosurgery both of the electrodes are active and hence serve as working tools.

One of the most urgent problems in surgery up till now is a reliable, quick and high-quality arrest of bleeding in traumatic lesions of tissues, especially parenchymatous ones, such as the liver, kidney, spleen, and the like, as well as the arrest of bleeding from major blood vessels during preplanned surgical procedures.

Known in the present state of the art is a wide variety of bipolar electrosurgical instruments, e.g., forceps, in particular those for blood vessel coagulation (cf., e.g., an advertisement prospectus "Chirrurgie Zubehör ERBE elektromedizinsche Geräte").

Such instruments consist largely of two arms insulated from each other and provided with current-cunducting working jaws which are for catching blood vessels, while high-frequency current is supplied to both of the arms. However, such instruments fail to reliably catch and grip a blood vessel seated deeply in the parenchyma upon its contraction after having been severed, while any further attempt to catch the vessel inflicts mechanical damage upon still greater areas of the surrounding tissues.

Moreover, said instruments produce a large coagulation-affected area of tissues surrounding the vessel operated upon, and the coagulated tissue or thrombus that has stuck to the instrument working surface, is liable to be torn away when withdrawing the instrument after caogulation.

In addition, the instruments discussed above fail to simultaneously expose bloodlessly and catch mechanically and reliably a nonopened vessel seated deeply in the bulk of a parenchymatous organ.

SUMMARY OF THE INVENTION

It is a primary and essential object of the present invention to provide such a bipolar electrosurgical instrument that would enable one to perform surgery on the parenchymatous tissues and different-calibre blood vessels quickly and with a high quality.

The object is accomplished due to the fact that in a bipolar electrosurgical instrument, comprising arms insulated from each other and provided with current-conducting workking jaws, according to the invention, the working jaws are shaped as prongs curved in the same direction, and the working jaw of one of the arms is made as a fork.

Such a constructional arrangement of the instrument makes possible quick and high-quality surgical procedures on the parenchymatous tissues.

It is practicable to set the arms of the instrument parallel to each other and to make the working jaws traversable with respect to each other in the longitudinal direction of the arms.

This feature enables one to fuse the lumens of nonopened vessels of any calibre over any preset length.

The curved prong of one of the arms may be longer than the fork prongs of the other arm.

This provides for reliable catching of a vessel deeply in the parenchymatous tissue and its movement.

The surface area of the single prong may be equal to the total surface area of the fork prongs.

This provides for high-quality coagulation of the caught living tissues.

The surface area of the single prong may be less than that of the fork prongs.

This makes it possible to cut through the tissues being gripped.

BRIEF DESCRIPTION OF THE DRAWINGS

In what follows the electrosurgical instrument of the invention will now be disclosed in a detailed description of some specific illustrative embodiments thereof given by way of example with reference to the accompanying drawings, wherein.

BEST MODE OF CARRYING OUT THE INVENTION

Figure 1:
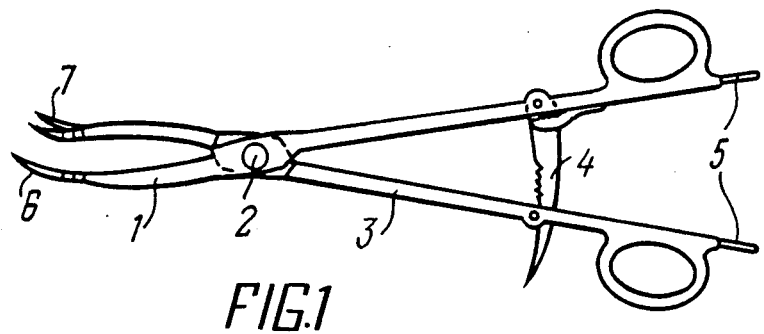
FIG. 1 is a general schematic view of a bipolar electrosurgical instrument, according to the invention.
Figure 2:
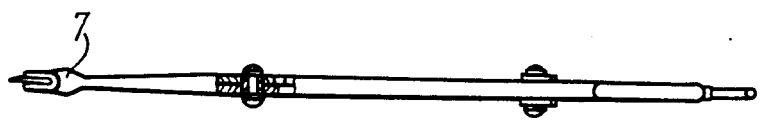
FIG. 2 is a plan view of the bipolar electrosurgical instrument of FIG. 1.
Figure 4:
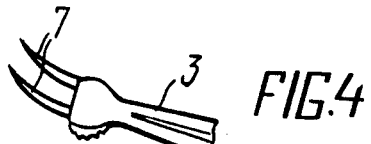
FIG. 4 illustrates a current-conducting working jaw of the other arm of the bipolar electrosurgical instrument whose prongs constitute a fork, according to the invention.
Figure 3:
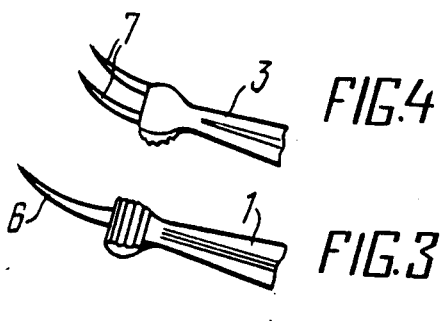
FIG. 3 illustrates a current-conducting working jaw of one arm of the bipolar electrosurgical instrument, shaped as a single prong, according to the invention.
Figure 5:
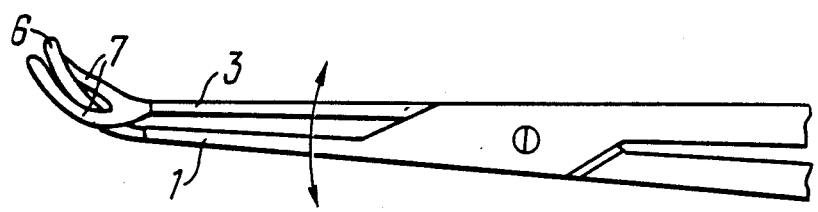
FIG. 5 illustrates the position of the current-conducting working jaws of the electrosurgical instrument with its arms brought together, according to the invention.

The bipolar electrosurgical instrument of the invention comprises a current-conducting electrically insulated arm 1 (FIGS. 1 and 2), which is joined, through a nonconductive pin 2, to another current-conducting electrically insulated arm 3. A restrictor 4 is provided on the arm 3 to limit the instrument expansion angle. Each of the arms 1 and 3 is provided with leads 5 for high-frequency current to supply and has working jaws which are shaped, in a given particular case, as prongs 6 and 7, respectively. The arm 1 terminates in the prong 6 (FIG. 3) insulated electrically at the place of contact with the prongs 7 of the other arm 3. The prongs 7 of the arm 3 constitute a bifurcation of two-pronged fork (FIG. 4). With the arms 1 and 3 brought together (FIG. 5) the prong 6 partially passes through and extends between the prongs 7. The prongs 6 and 7 are curved in the same direction.

Figure 6:
FIG. 6 is a plan view of the current-conducting working jaws made in the form of prongs in an embodiment of the instrument, wherein the surface area of a single prong equals the surface area of both prongs of the fork, according to the invention.

The curved prong 6 of the arm 1 is expedient to be longer than the fork prongs 7 of the other arm 3, while the surface area of the prong 6 (FIG. 6) may be equal to a total surface area of the fork prongs 7. As it is commonly known, reliable coagulation of blood vessel 8 and living tissues can be provided only when the active electrodes (that is, the prongs 6 and 7 in this particular case) of a bipolar electrosurgical instrument are equal in area.

Figure 7:
FIG. 7 is a plan view of the current-conducting working jaws made in the form of prongs in an embodiment of the instrument, wherein the surface area of a single prong is less than the surface area of both prongs of the fork, according to the invention.

However, the surface area of the prong 6 may be smaller than a total surface area of the fork prongs 7 (FIG. 7).

Such a constructional arrangement of the current-carrying working jaws of the electrodes makes it possible to cut through the tissues being caught, since the energy evolved on the working jaws is inversely proportional to their surface area. In addition, such a construction of the current-carrying jaws enables one to cut through the tissues of hollow organs, e.g., the gastric wall, the vesical wall, etc.

Figure 8:
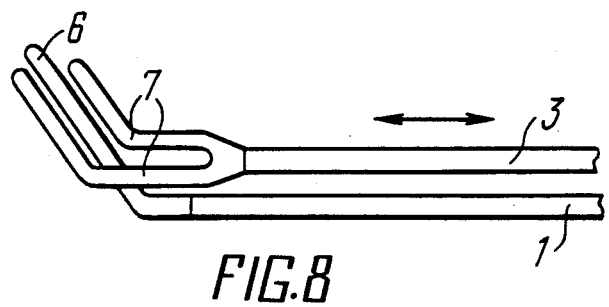
FIG. 8 is a general schematic view of one of the embodiments of the bipolar electrosurgical instrument featuring parallel arranged arms, according to the invention.
Figure 9:
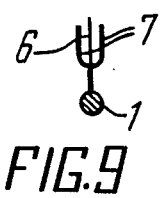
FIG. 9 is an end view (from the ends of the prongs) of the embodiment of the bipolar electrosurgical instrument with parallel arranged arms as shown in FIG. 8, according to the invention.

The insulated arms 1 and 3 may be arranged parallel to each other (FIG. 8). Such being the case, the working jaws of these arms shaped as the prongs 6 and 7, are capable of traversing with respect to each other (FIG. 9) in the longitudinal direction of the arms.

Figure 10:
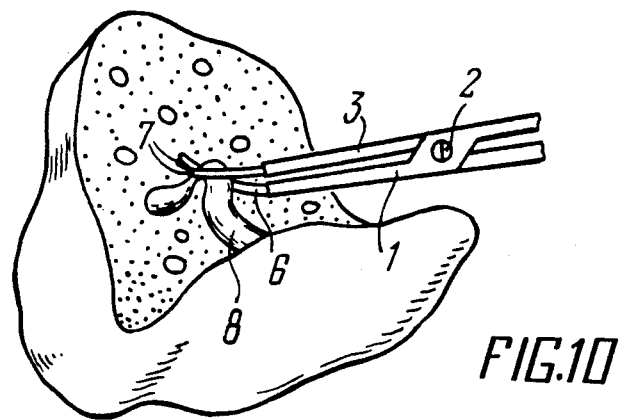
FIG. 10 illustrates schematically a working step of the electrocoagulation procedure applied to a nonopened blood vessel in the gape of a wound deeply in the living tissues, according to the invention.
Figure 11:
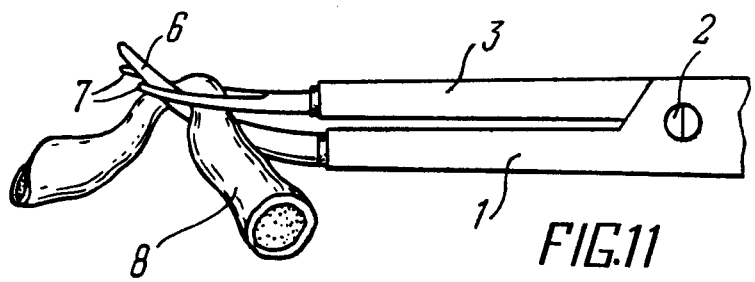
FIG. 11 illustrates schematically a working step of the electrocoagulation procedure applied to a mobilized nonopened vessel, according to the invention.

For the sake of simpler understanding the functioning of the electrosurgical instrument of the present invention will now be described with reference to electrocoagulation applied to a nonopened blood vessel in the gape of an operative wound (FIGS. 10, 11). The procedure is carried out as follows.

The prong 6 of the arm 1 is used as a guide prong for mechanical liberation of an intact (nonopened) blood vessel 8 in the operative wound. Once the intact vessel 8 has been liberated, the prong 6 is placed thereunder.

Once the arms 1 and 3 are brought together the liberated vessel 8 is caught by the prong 6 and the fork 7, whereupon a high-frequency current is applied to the current leads 5. Once the surgery has been completed, the instrument is withdrawn from the operative wound having preliminarily brought the arms 1 and 4 apart as far as the restrictor 4.

The aforedescribed bipolar electrosurgical instrument is most efficaciously applicable for coagulation of intact blood vessels with a calibre of from a few fractions of a millimeter to about 3 mm. The instrument inflicts mechanical and electrocoagulation damage to the living tissues surrounding the vessel involved, but within a small area.

Figure 12:
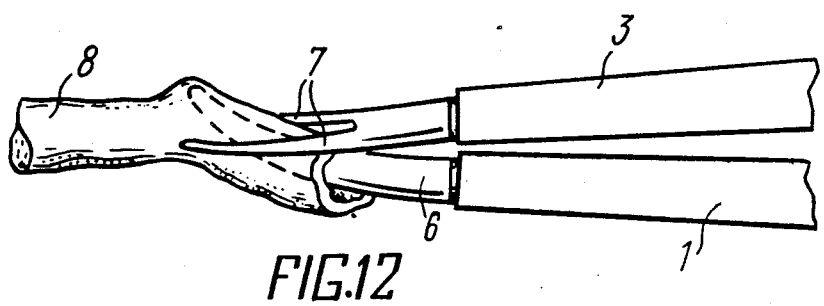
FIG. 12 illustrates schematically a working step of the electrocoagulation procedure (intra- and extravasal) applied to an open vessel deeply in the parenchyma, according to the invention.

Now there will be considered an exemplary procedure for intra-extravasal coagulation of an open blood vessel lying deeply in the parenchyma (FIG. 12).

The procedure is performed as follows.

Before surgery the arms 1 and 3 of the instrument must be brought apart as far as the restrictor 4. The prong 6 is inserted into the lumen of a medium-calibre blood vessel. The bifurcated prongs 7 of the arm 3 are introduced into the hepatic parenchyma above the vessel being operated. Once the arms 1 and 3 have been brought together, the vessel wall is subjected to mechanical deformation by being tightly pressed by the prongs 7 against the prong 6, whereupon high-frequency current is supplied along the current leads 5. After coagulation of the vessel the arms 1 and 3 are brought apart as far as the restrictor 4, and the instrument is withdrawn, in the set-together state, from the operative wound. The bipolar electrosurgical instrument, wherein the prongs 6 and 7, when brought together, intersect at an angle and a positive interference, thus providing for reliable holding of the stumps of the vessels 8 having a calibre of from a few fractions of a millimeter to about 8 mm but inflicting traumatic lesion upon the living tissues, predominantly hepatic, splenic, renal, and others.

Figure 13:
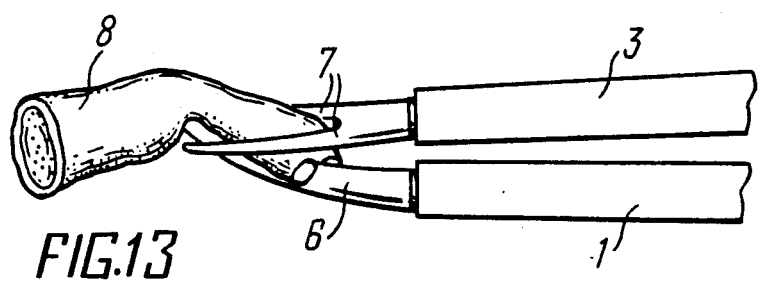
FIG. 13 illustrates schematically a working step of the electrocoagulation procedure (intra- and extravasal) applied to an open vessel deeply in the parenchyma, according to the invention.

Further, the operation of the electrosurgical instrument will be described with reference to an extra-extravasal electrocoagulation procedure applied to an open blood vessel seated deeply in the parenchyma (FIG. 13).

Before surgery the arms 1 and 3 are to be set apart as far as the restrictor 4. Then the prong 6 is introduced into the parenchyma close to the wall of the large-calibre bleeding vessel 8, and the bifurcated prongs 7 of the arm 3 are introduced into the hepatic parenchyma above the vessel 8. Next the arms 1 and 3 are bought together and the gripped walls of the vessel 8 are approximated to each other and pressed tightly against the prongs 6 and 7 of the instrument, whereupon high-frequency current is supplied along the current leads 5. The electrocoagulation procedure being completed, the h.f. current is disconnected, the arms 1 and 3 are set apart as far as the restrictor 4, and the instrument is withdrawn in the set-apart state.

When electrocoagulation is carried out using the electrosurgical instrument of the invention featuring the parallel arranged arms 1 and 3 (FIGS. 8 and 9), drawing the working jaws (shaped as the prongs 6 and 7) together causes the prongs 7 to exert mechanical pressure upon the vessel 8. Then the prongs 7, while sliding on both sides of the prong 6, displace the blood from the interior of the vessel 8 at the place of intended vessel fusion. In this case the working jaws of the arms 1 and 3 travel in a longitudinal direction and parallel to each other.

Figure 14:
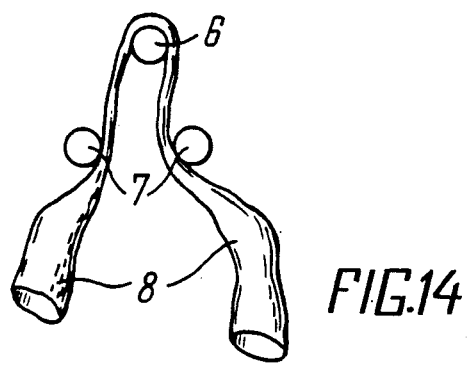
FIG. 14 is a schematic view of a mutual arrangement of the instrument prongs and the vessel being operated in an embodiment of the electrosurgical instrument having its arms arranged in parallel to each other, according to the invention.

Depending on a required length of the vessel 8 segment to be fused (which is larger as the calibre of the vessel 8 itself is larger), the central prong 6 is passed in between the fork prongs 7 and is pulled along with the vessel 8 for a shorter or longer distance (see FIG. 14). As it has been mentioned hereinabove, the greater the calibre of the vessel being fused the larger is the bloodless segment thereof required for fusion, and hence the greater the distance the prong 6 and the vessel 8 gripped thereby should be extended relative to fork prongs. All the steps described above are easy and simple to perform by the electrosurgical instrument in question when provided with the parallel arranged arms 1 and 3. As it is evident from FIG. 14, the length of the vessel segment being fused depends upon the bloodless vessel portion which is pulled by he single prong 6 into the fork formed by the two other prongs 7. The aforesaid length corresponds to about double the distance from the central prong 6 to either of the fork prongs 7.

As it has already been noted hereinbefore, reliable fusion together of the vessel opposite walls by virtue of high-frequency currents may be carried out only when the lumen of the vessel segment being fused is bloodless. Therefore, whenever it is necessary to reliably fuse a vessel having a calibre of about 4 mm, the length of its bloodless portion should be 6 mm, accordingly; when the vessel calibre equals 8 mm the length of its bloodless segment must be about within 10 and 12 mm, and so on. The length of the vessel portion to be fused is adjustable by the surgeon's one hand conveniently and reliably within an adequately broad range and without resorting to any auxiliary appliances or instruments.

The central prong 6 is expedient to be longer than the fork prongs 7. This renders the electrosurgical instrument of the invention more convenient and reliable in operation, since it enables one to easily catch a required tissue or the exposed blood vessel 8.

INDUSTRIAL APPLICABILITY

Thus, provision of the working jaws of the instrument in the form of prongs curved in the same direction makes it possible to reliably catch a blood vessel of any calibre deeply in the parenchymatous tissue, effective blood displacement out of the interior of the exposed vessel at the place of an intended fusion, and reliable fusion of the lumen of nonopened blood vessel of any calibre, large-calibre vessel inclusive, which remain in this case, which are not damaged mechanically due to the absence of the so-called "scissors effect". Furthermore, the lumen of a nonopened blood vessel can be fused over any preset length, with a minimum area affected by electrocoagulation necrosis and minimum mechanical damage to the vessel surrounding tissues.

I claim:

1. A bipolar electrosurgical instrument, said instrument comprising:
   (a) a first arm terminating in a unitary curved, electrically conductive prong extending outwardly from an end thereof, said unitary prong having a narrowed end for liberating an intact blood vessel from a wound and for insertion into a lumen of an open blood vessel;
   (b) a second arm connected to said first arm for movement relative to said first arm and terminating in a pair of laterally spaced, outwardly extending curved, electrically conductive prongs defining a two pronged fork, said first and second arms being electrically insulated from each other and movable relative to each other to cause said unitary prong to pass into and through the space between said pair of prongs, each of said prongs being curved in the same direction; and
   (c) conductor means for electrically connecting said prongs with a source of electrical energy for coagulating a blood vessel positioned between said unitary prong on said first arm and said pair of prongs on said second arm.

2. A bipolar electrosurgical instrument as claimed in claim 1, wherein the unitary curved prong of one of the arms is longer than the two pronged fork of the other arm.

3. A bipolar electrosurgical instrument as claimed in claim 1, wherein the surface area of the unitary prong is substantially equal to the sum of the surface areas of the two pronged fork.

4. A bipolar electrosurgical instrument as claimed in claim 1, wherein the surface area of the unitary prong is less than the sum of the surface areas of the two pronged fork.

5. A bipolar electrosurgical instrument, comprising: two electrically conducting arms connected to each other for relative movement therebetween and electrically insulated from each other and having ends carrying respective conductive working jaws in the form of prongs bent in one and the same direction, the working jaw of one of said arms comprising a double prong yoke and the working jaw of the other of said arms including a single prong, the prongs of said double prong yoke of one of said arms lying outwardly of and on opposite sides of said single prong of the working jaw of the other arm when said arms are brought close to each other.

6. A bipolar electrosurgical instrument according to claim 5, said single prong of one said working jaw being longer than said prongs of the other working jaw.

7. A bipolar electrosurgical instrument according to claim 5, wherein the surface area of said single prong is substantially equal to the total surface area of said double prong of the yoke.

8. A bipolar electrosurgical instrument according to claim 5, wherein said single prong has a surface area which is smaller than the total surface area of said double prong of the yoke.

* * * * *